(12) United States Patent
Wong et al.

(10) Patent No.: US 6,183,466 B1
(45) Date of Patent: Feb. 6, 2001

(54) DOSAGE FORM COMPRISING A CAPSULE

(75) Inventors: Patrick S. L. Wong, Burlingame; Felix Theeuwes, Los Altos Hills; Vincent J. Ferrari, Foster City; Liang C. Dong, Sunnyvale, all of CA (US)

(73) Assignee: Alza Corporation, Mountain View, CA (US)

( * ) Notice: Under 35 U.S.C. 154(b), the term of this patent shall be extended for 0 days.

(21) Appl. No.: 09/344,811

(22) Filed: Jun. 25, 1999

Related U.S. Application Data

(60) Provisional application No. 60/097,390, filed on Aug. 21, 1998.

(51) Int. Cl.[7] .............................. A61K 9/48; A61K 9/22
(52) U.S. Cl. .................. 604/892.1; 424/451; 424/452; 424/453
(58) Field of Search ..................... 424/451, 452, 424/453; 604/892.1

(56) References Cited

U.S. PATENT DOCUMENTS

| | | | |
|---|---|---|---|
| 3,916,899 | 11/1975 | Theeuwes et al. | 128/260 |
| 4,627,850 | 12/1986 | Deters et al. | 604/892 |
| 5,324,280 | 6/1994 | Wong et al. | 604/892.1 |
| 5,614,578 | 3/1997 | Dong et al. | 524/377 |

*Primary Examiner*—Thurman K. Page
*Assistant Examiner*—Amy E. Pulliam
(74) *Attorney, Agent, or Firm*—John A. Dhuey; Steven F. Stone

(57) ABSTRACT

A dosage form is disclosed comprising a wall that defines an injection-molded compartment housing a capsule comprising a drug formulation.

7 Claims, 3 Drawing Sheets

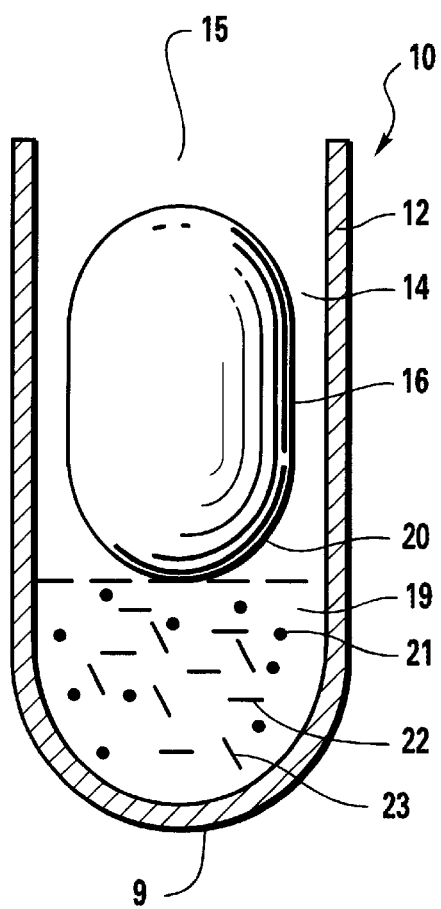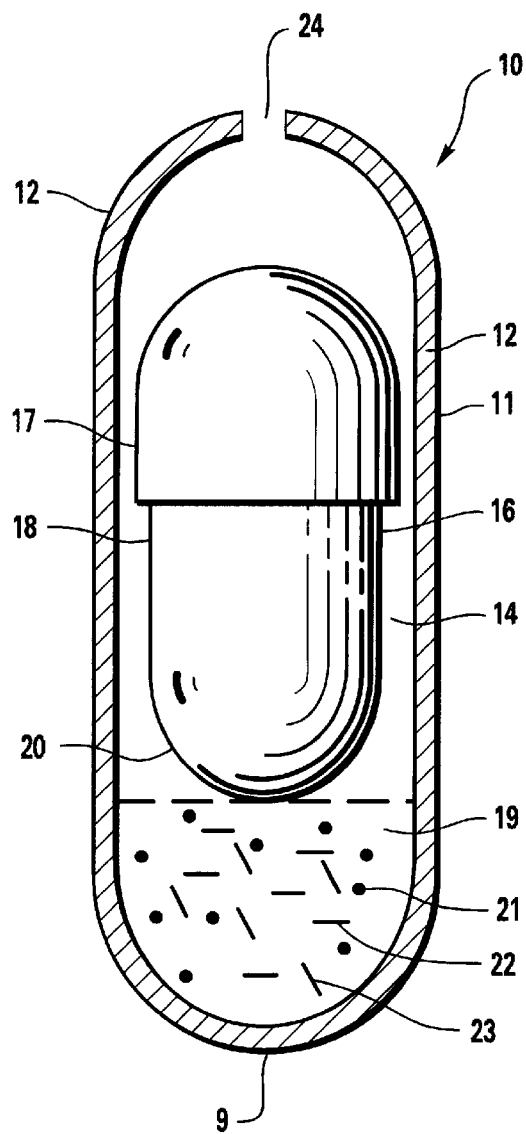
FIGURE 3
FIGURE 4

DOSAGE FORM COMPRISING A CAPSULE

CROSS-REFERENCE TO RELATED APPLICATIONS

This application claims the benefits of provisional application Serial No. 60/097,390 filed on Aug. 21, 1998.

FIELD OF THE INVENTION

This invention pertains to a controlled-release dosage form. More particularly, the invention relates to a dosage form comprising a wall encapsulating a space for holding and storing a capsule. The invention concerns also (1) a process for providing a controlled-release dosage form comprising a wall that defines a space for housing an internal capsule, and (2) a process for converting a non-controlled drug releasing capsule into a controlled-release dosage form.

BACKGROUND OF THE INVENTION

Capsules are dosage form in which a composition comprising a drug is enclosed within a wall. Capsules are a popular method for administering a drug in both prescription practice and in over-the-counter practice. Capsules are used widely in hospitals, nursing homes, retirement centers, homes, and in other environments, such as the military and naval environments. Capsules enjoy this popularity because they are tasteless, essentially innocuous, easily administered, easily filled extemporaneously, and they can be manufactured in large numbers. Additionally, some capsule users find it easier to swallow capsules than other dosage forms, such as a solid tablet.

While the above advantages and patient preference contribute to the continuing acceptance of capsules, there are certain shortcomings associated with capsules. For example, after oral administration, capsules give up all their useful drug immediately. That is, capsules are dose-dumping dosage forms. The therapeutic consequence of this dose-dumping is non-controlled therapy consisting of an initially high dose of drug, followed by a total absence of drug between later administered capsules. For many drugs, this form of administration can have undesirable therapeutic effects, especially if the drug has a low therapeutic index and is not suited to time-varying rates of administration. Another shortcoming associated with capsules is they are poorly suited for administering drugs with short biological half-lives, and this results in exclusion of large drugs including mammalian biochemicals, natural hormones, humoral factors, and the like.

Yet another shortcoming associated with capsules is their instant delivery and its accompanying detrimental effects. Because of this inherency, capsules require a high frequency of use, and this can lead to a failure of patient compliance for a prescribed dosage schedule. Such failures are reflected in a lack of therapeutic effectiveness, and in possible toxic effects. The latter effects can occur when patients double or triple their dosage to compensate for their prior omissions. Faulty non-compliance associated with the use of capsules is a common and largely ignored problem.

It will be appreciated by those versed in the drug delivery art in the light of this presentation that if a dosage form is provided comprising a capsule that is essentially free of the tribulations known to the prior art, such a dosage form comprising a capsule would have a positive therapeutic value and it would also represent an unexpected advancement in the drug delivery art. The present invention advances the state of the drug delivery art by providing a dosage form manufactured to house a capsule for optimizing the therapeutic effects of a drug. The dosage form comprising the capsule administers a drug at a controlled rate for a prescribed period of time. The dosage form provides continuous control over the administration of the drug, and it maintains this control over an extended period of time.

OBJECTS OF THE INVENTION

Accordingly, it is an immediate object of this invention to provide a dosage form comprising a capsule for delivering a drug at a controlled rate over a sustained period of time, which dosage form represents both an unexpected improvement and an unexpected advancement in the drug delivery art.

Yet another object of the invention is to provide a dosage form comprising a capsule which capsule comprises a solution, oil, emulsion, sol or suspension, that can be delivered by the dosage form at a programmed, controlled rate over a prolonged period of time.

Yet another object of this invention is to provide a dosage form comprising a capsule, which capsule comprises a composition in solid form selected from the group consisting of solid, powdered, pulverized, micronized and particle form, which forms in the presence of fluid imbibed into the dosage form forms a solution or a suspension that is delivered by the dosage form in a sustained-release period up to twenty-four hours.

Yet another object of this invention is to provide a dosage form comprising a capsule, which dosage form is simple in construction and exhibits all the practical benefits of controlled and continuous administration of a drug formulation during the dosage form's residency in a biological environment of use over a prolonged period of time up to twenty-four hours.

Yet another object of this invention is to provide a dosage form for administering a drug in the gastrointestinal tract by making available a dosage form that maintains its integrity in the gastrointestinal tract during its complete transit therethrough.

Yet another object of this invention is to provide a dosage form comprising a wall that envelopes a space for receiving a capsule, which capsule comprises a drug formulation that includes a pharmaceutically acceptable carrier, and which drug can be delivered by the dosage form at meaningful and therapeutic rates over a prolonged period of time.

Yet another object of the invention is to provide a dosage form comprising a composition comprising an expandable hydrogel.

Yet another object of the invention is to provide a dosage form comprising a wall that comprises a semipermeable composition, which wall encapsulates an internal placed capsule comprising a drug formulation.

Yet another object of the invention is to provide a dosage form comprising both a capsule and a composition comprising an expandable hydragel for displacing the contents of the capsule from the dosage form.

Yet another object of the invention is to provide a process for converting a non-controlled capsule into a controlled-release dosage form.

Yet another object of the invention is to provide a process for providing a dosage form comprising an exterior wall that defines an internal space for storing and holding a capsule.

Yet another object of the invention is to provide a process for manufacturing a dosage form, wherein the process comprises shaping a wall to define an internal compartment that functions as a space for receiving a capsule, which dosage form comprises a closed-end and an opened-end, placing a capsule comprising a drug formulation in the compartment, and closing the opened-mouth end while simultaneously providing an orifice in the dosage for delivering the drug formulation from the dosage form to a patient in need of therapy.

Other objects, features, aspects and advantages of the invention will be more apparent to those versed in the drug delivery art from the following detailed specification taken in conjunction with the drawings and the accompanying claims.

BRIEF DESCRIPTION OF DRAWINGS

In the drawing figures, which are not drawn to scale but are set forth to illustrate embodiments of the invention, the drawing figures are as follows:

Drawing

Drawing

Drawing FIG. 3 is an opened view of the dosage form of drawing FIG. 1, wherein the dosage form holds and stores a capsule made as a one-piece capsule that contains a drug formulation;

Drawing FIG. 4 is an opened view of the dosage form of drawing FIG. 1 illustrating the previously wide-opened mouth of drawing FIG. 1 crimped in a closed position while simultaneously providing an orifice for delivering a drug formulation from the dosage form;

Drawing

In the drawings, and in the specification, like parts in related figures are identified by like numbers. The terms appearing earlier in the specification, and in the description of the examples are defined later in the specification.

DETAILED DESCRIPTION OF THE DRAWINGS AND INVENTION

Figure 1:
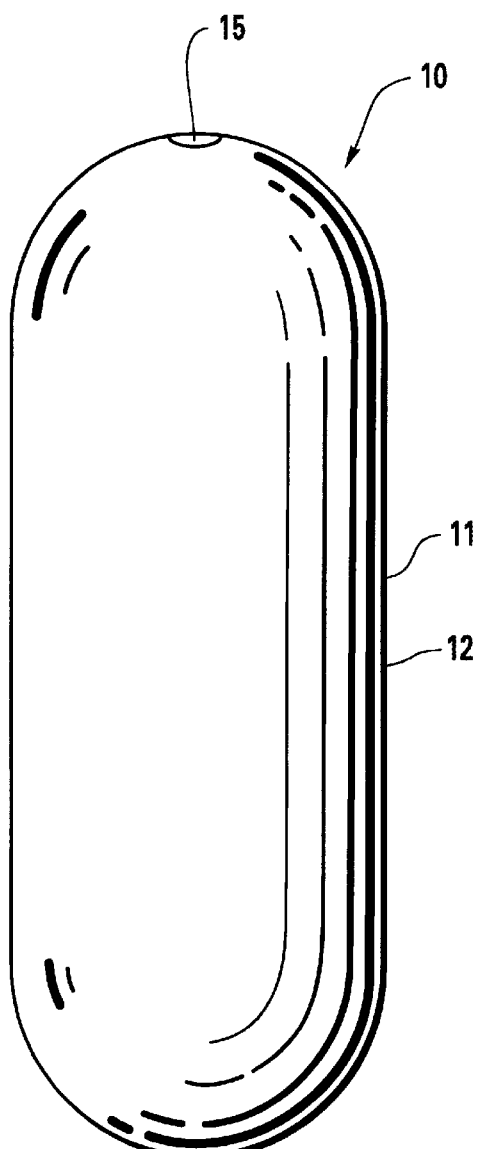
FIG. 1 is a general view of a dosage form provided by the invention.

Turning now to the drawings in detail, which are examples of various dosage forms provided by the invention, and which examples are not to be construed as limiting, one example of a dosage form is seen in drawing FIG. 1. In drawing FIG. 1, a dosage form 10 is seen comprising a body member 11, comprising a wall 12, surrounding an internal compartment or internal space, not shown, and at least one orifice 13 for releasing a therapeutic drug formulation from dosage form 10.

Figure 2:
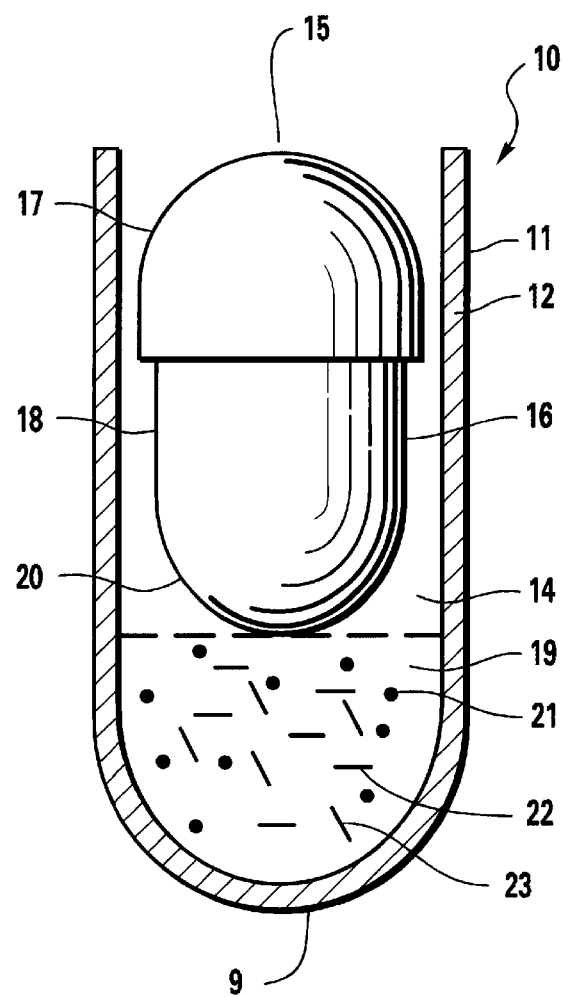
FIG. 2 is an opened view of the dosage form of drawing FIG. 1, wherein the dosage form comprises a capsule made of two parts comprising a body portion telescopically capped by an engaging cap portion.

In drawing FIG. 2, dosage form 10 is seen in opened section. In drawing FIG. 2, dosage form 10 comprises a body member 11, a wall 12, that surrounds and forms an internal compartment or internal space 14, that communicates with the exterior of dosage 10 through an opened wide-mouth 15. Mouth 15, in dosage form 10 is initially manufactured, comprising a width equal to the internal side-to-side dimension of dosage form 10. Wall 12 comprises an injection-molding composition that is shaped into dosage form 10. Wall 12 forming compositions is permeable at least in part to the passage of an aqueous fluid and it comprises a thermoplastic polymer, or the compositions comprise a mixture of thermoplastic polymers and optional injection-molding ingredients. The thermoplastic polymer that can be used for the present purpose comprise polymers that have a low softening point, for example, below 200° C., preferably within the range of 400° C. to 180° C. The polymers, are preferably synthetic resins, for example, linear polycondensation resins, condensation polymerized resins, addition polymerized resins, such as polyamides, resins obtained from diepoxides and primary alkanolamines, resins of glycerine and phthalic anhydrides, polymethane, polyvinyl resins, polymer resins with end-positions free or esterified carboxyl or carboxamide groups, for example with acrylic acid, acrylic amide, or acrylic acid esters, polycaprolactone, and its copolymers with dilactide, diglycolide, valerolactone and decalactone, a resin composition comprising polycaprolactone and polyalkylene oxide, and a resin composition comprising polycaprolactone, a polyalkylene oxide such as polyethylene oxide, poly (cellulose) such as poly(hydroxypropylmethylcellulose), poly(hydroxyethymethylcellulose), and poly (hydroxypropylcellulose). The membrane forming composition can comprise optional membrane-forming ingredients such as polyethylene glycol, talcum, polyvinylalcohol, lactose, or polyvinyl pyrrolidone. The compositions for forming an injection-molding polymer composition can comprise 100% thermoplastic polymer. The composition in another embodiment comprises 10% to 99% of a thermoplastic polymer and 1 % to 70% of a different polymer with the total equal to 100%. The invention provides also a thermoplastic polymer composition comprising 1% to 98% of a first thermoplastic polymer, 1% to 90% of a different, second polymer and 1% to 90% of a different, third polymer with all polymers equal to 100%. Representation composition comprises 20% to 90% of thermoplastic polycaprolactone and 10% to 80% of poly(alkylene oxide); a composition comprising 20% to 90% polycaprolactone and 10% to 60% of poly(ethylene oxide) with the ingredients equal to 100%; a composition comprising 10% to 97% polycaprolactone, 10% to 97% poly(alkylene oxide), and 1% to 97% of poly(ethylene glycol) with all ingredients equal to 100%; a composition comprising 20% to 90% polycaprolactone and 10% to 80% of poly(hydroxypropylcellulose) with all ingredients equal to 100%; and a composition comprising 1% to 90% polycaprolactone, 1% to 90% poly(ethylene oxide), 1% to 90% poly(hydroxypropylcellulose) and 1% to 90% poly (ethylene glycol) with all ingredients equal to 100%. The percent, expressed is weight percent, wt %. The wall 12 forming compositions can comprise additionally 10% to 90% caprolactone-lactide copolymer and 10% to 80% polyalkylene with the composition equal to 10%; a composition comprising 10 to 90% caprolactoneglycolic copolymer and 10% to 90% polyalkylene oxide with the composition equal to 100%; a composition comprising 10% to 90% caprolactone-lactide copolymer, 10% to 50% polyalkylene oxide, and 10% to 50% poly(ethylene glycol copolypropylene glycol) with the composition equal to 100%; and a composition comprising 20% to 90% polycaprolactone and 10% to 80% ethylene vinylacetate copolymer, for injection-molding a polymer composition wall for manufacturing therapeutic dosage form 10. The polymeric compositions are disclosed in U.S. Pat. No. 5,614,578 issued to inventors Dong, Wong, Pollock, and Ferrari.

Dosage form 10, as seen in drawing FIG. 2, comprises in internal space 14 and a capsule 16. Capsule 16 is composed of two parts, a cap 17 and a receiving body 18, which are fitted together after the larger body 18 is filled with a preselected appropriate drug formulation. This is done by slipping or telescoping the cap section 17 over the body section 18, thus completely surrounding the therapeutic agent formulation. Two-piece capsules are made by dipping stainless steel molds into a bath containing a solution of a capsule lamina-forming material to coat the mold with the material. Then, the molds are withdrawn, cooled, and dried in a current of room temperature air 22.50° C. The capsule is stripped from the mold and trimmed to yield a lamina with an internal member. The engaging cap 17 that telescopically caps the drug formulation receiving body member 18 is made in a similar manner. Then, the closed and filled capsule is placed inside dosage form 10 in internal space. In another embodiment, the capsule 16 can be made with each part 17 and 18 having matched locking rings near their opened ends that permit joining and locking together the overlapping cap 17 and receiving body 18, after filling 18 with a drug formulation. In this embodiment, a pair of matched locking rings are formed into cap portion 17 and body portion 18, and these rings provide the locking means for securely holding together the capsule. The capsule can be filled manually with a drug formulation, or capsule 16 can be machine-filled with the drug formulation. The word "capsule" as used herein denotes its art-accepted meaning of a wall, lamina, or a membrane enclosing a drug formulation.

Dosage form 10 houses an expandable composition 19 distant from mouth 15 and initially separate and in contact with end 20 of capsule 16. Composition 19 is a driving force that acts in cooperation with dosage form 10 and capsule 16 for delivering a drug formulation from dosage form 10. Composition 19 exhibits fluid absorbing and/or fluid imbibing properties. Composition 19 comprises a hydrophilic polymer that can interact with water and aqueous biological fluids imbibed into dosage form 10 and then swell or expand. The hydrophilic polymers 21 are known also as osmopolymers, hydrogels and osmogels as they exhibit a concentration gradient across wall 12, and thereby absorb or imbibe fluid into dosage form 10. Representative of osmopolymers 21 are poly(ethylene oxide) having a 750,000 to 10,000,000 weight average molecular weight, and, an alkali carboxymethylcellulose of 10,000 to 6,000,000 weight average molecular weight such as sodium carboxymethylcellulose. Composition 19 comprises 10 mg to 475 mg of hydrophilic polymer 21. Composition 19 can comprise additionally 1 mg to 75 mg of poly(cellulose) 22, a member selected from the group consisting of hydroxyethylcellulose, hydroxypropylcellulose, hydroxypropylmethylcellulose, and hydroxypropylbutylcellulose. Driving force composition 19 comprises 0.5 mg to 175 mg of an osmotically effective solute 23, known also as osmagents, that imbibe fluid through wall 12 into dosage form 10. The osmotically effective solutes are selected from the group consisting of salt, acid, amine, ester and carbohydrate as represented by a member selected from the group consisting of magnesium sulfate, magnesium chloride, potassium sulfate, sodium sulfate, lithium sulfate, potassium acid phosphate, mannitol, urea, inositol, magnesium succinate, tartaric acid, sodium chloride, potassium chloride, and carbohydrates such as raffinose, sucrose, glucose, lactose, and sorbitol. Composition 19 optionally comprises 0 wt % to 3.5 wt % of a colorant such as ferric oxide. The total weight of all components in composition 19 is equal to 100 wt %.

Dosage form 10, when in operation in a fluid environment of use, such as the gastrointestinal tract of a human, imbibes fluid through wall 12 into dosage form 10, thereby causing capsule wall 16 to open and release its drug formulation into compartment 14. Also, when dosage form 10 is in operation, fluid is imbibed into composition 19 thereby causing composition 19 to absorb the imbibed fluid and expand to produce a driving force that pushes against drug formulation in compartment 14. These chemical/physical actions cause the displacement of drug formulation from dosage form 10.

In drawing FIG. 3, dosage form 10 is seen in opened view. Dosage form 10 in FIG. 3 comprises an exterior wall 12 that surrounds and forms an internal compartment 14. Dosage form 10 comprises a closed end 9 distant from a mouth 15 or an opened end. Wall 12 comprises an injection-molded composition as described in FIG. 2. Dosage form 10 in FIG. 3 contains a one-piece capsule 16. The one-piece capsule 16 is of sealed construction that encapsulates a drug formulation thereon. The one-piece capsule 16 is made by various processes, including the plate process, the rotary die process, the reciprocating die process, and the continuous process. The plate process uses a set of molds. A warm sheet of a prepared capsule lamina-forming material is laid over the lower mold and the agent formulation poured on it. A second sheet of the lamina-forming material is placed over the agent formulation followed by the top mold. The mold set is placed under a press and a pressure applied, with or without heat to form a unit, soft capsule. The capsules are washed with a solvent for removing excess agent formulation from the exterior of the capsule, and the capsule is then air-dried at room temperature, about 22.50° C.

The rotary die process uses two continuous films of capsule lamina-forming material that are brought into convergence between a pair of revolving dies and an injector wedge. The process fills and seals the capsule in dual and coincident operations. In this process, the sheets of capsule lamina-forming material are fed over guide rolls, and then down between the wedge injector and the die rolls. The agent formulation to be capsuled flows by gravity into a positive displacement pump. The pump meters the agent formulation through the wedge injector and into the sheets between the die rolls. The bottom of the wedge contains small orifices lined up with the die pockets of the die rolls. The capsule is about half-sealed when the pressure of pumped agent formulation forces the sheets into the die pockets, wherein is the soft capsules are simultaneously filled, shaped, hermetically sealed and cut from the sheets of lamina-forming materials. The sealing of the soft capsule is achieved by mechanical pressure on the die rolls and by heating of the sheets of lamina-forming materials by the wedge. After manufacture, the agent formulation-filled capsules are dried in the presence of forced air, and placed into the dosage form.

The reciprocating die process produces soft capsules by leading two films of capsule lamina-forming material between a set of vertical dies. The dies as they close, open, and close perform as a continuous vertical plate forming row after row of pockets across the film. The pockets are filled with drug formulation, and as the pockets move through the dies, they are sealed, shaped, and cut from the moving film as capsules filled with agent formulation. The filled capsules 16 next are positioned in dosage form 10. The continuous process is a manufacturing system that also uses rotary dies, with the added feature that the process can successfully fill drug formulation in dry powder form into capsule 16, in addition to encapsulating liquids. Next, the capsule is placed into dosage form 10, free of lamination to the internal surface of wall 12. Procedures for manufacturing capsules are disclosed in U.S. Pat. No. 4,627,850, issued to inventors Deters, Theeuwes, Mullins and Eckenhoff.

In accordance with the practice of this invention, capsules 16 are made of tasteless materials that are filled easily, and they can have a variety of sizes from triple zero to five. The capsules used for the purpose of this invention can be transparent, colorless, or colored capsules can be used to give a special product a distinctive appearance. The capsules can be filled manually or by machine-filling methods. The capsule can be made from capsule forming materials comprising gelatin. Various gelatins can be used for this purpose, including gelatin having a viscosity of 15 to 30 millipoises and a bloom strength up to 150 grams; gelatin having a bloom value of 160 to 250; a composition comprising gelatin, glycerine, water and titanium dioxide; a composition comprising gelatin, erythrosin, iron oxide and titanium dioxide; a composition comprising gelatin, glycerine, sorbitol, potassium sorbate and titanium dixide; and a composition comprising gelatin, acacia, glycerine, and water. Materials useful for forming capsules are disclosed in U.S. Pat. No. 5,324,280 issued to inventors Wong, Theeuwes, Barclay and Dealey.

Dosage form 10 as seen in drawing FIG. 3 house an expandable composition 19 position at the bottom 20 of capsule 16. Composition 19 is described in drawing FIG. 2, which description is included in this description of FIG. 3.

Drawing FIG. 4 illustrates dosage form 10 wherein wall 12 was crimped inward to closed mouth 15 while retaining an orifice 24 in wall 12. Wall 12 is crimped by bending wall 12 inward manually or mechanically with applied 70° C. to 140° C. heat. The orifice 24 comprises a diameter of 0.025 mm to 7.5 mm. Maximum and minimum sizes for orifice 24 can be ascertained by procedures disclosed in U.S. Pat. No. 3,916,899, issued to inventors Theeuwes and Higuchi. The orifice, in the dosage form of this invention, comprises a diameter of 1 mil to 200 mil (0.025 to 0.05 mm).

Figure 5:
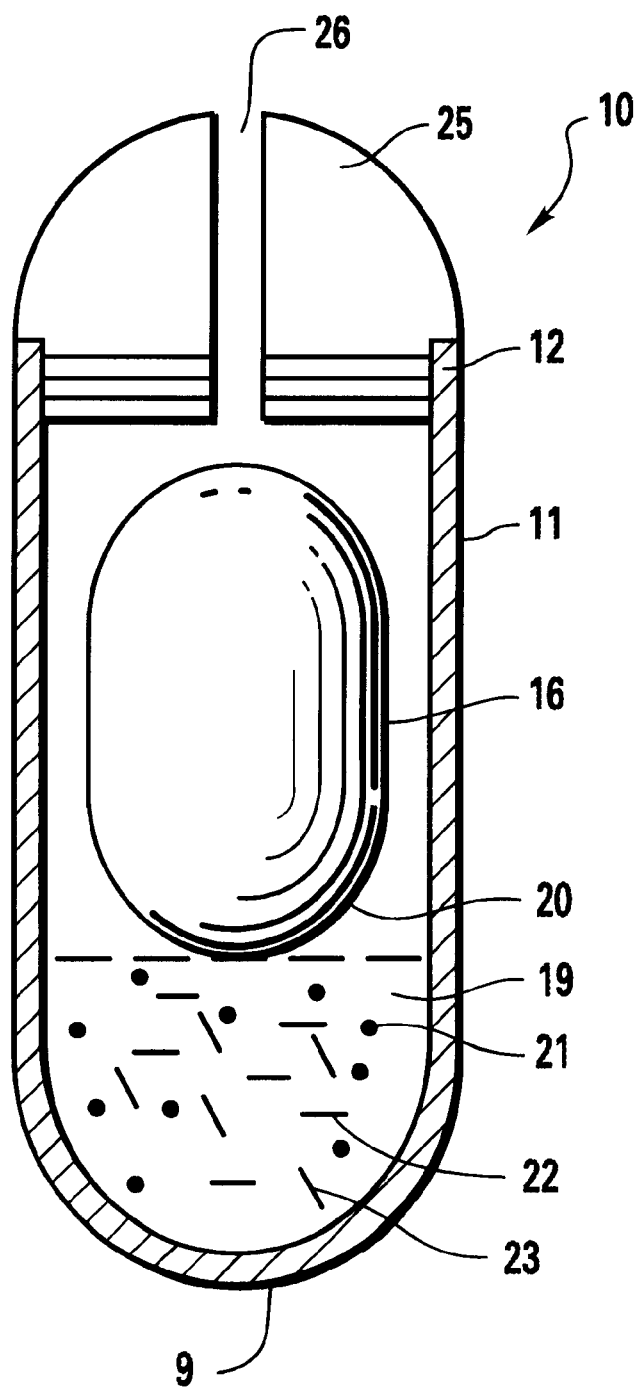
FIG. 5 is an opened view of the dosage form of drawing FIG. 1 illustrating the previously wide-opened mouth of drawing FIG. 1 closed by a snap-in cap that comprises an orifice for delivering a drug formulation from the dosage form.

Drawing FIG. 5 illustrates another embodiment for converting the opened mouth of dosage form 10 to an orifice of embracing lesser dimensions. In drawing FIG. 5, dosage form 10 comprises a snap-in cap 25 that comprises an orifice 26 therethrough. The snap-in cap 25 engages the internal surface of wall 12 while sealingly engaging the internal surface to close the initial mouth by friction. The friction concomitantly applies resistance to motion between the internal surface of wall 12 and snap-in cap 25. Snap-in cap 26 is a fitting for closing the end of dosage form 10 and it can be a single or two-piece design. An orifice 26 extends through snap-in cap 25 for releasing drug formulation from dosage form 10. The snap-in cap 25 can be made of a poly(olefin) such as high density poly(ethylene), poly (acrylonitrile), poly(acrylamide), aluminum, stainless steel, or ceramic.

The oral dosage form of the invention comprises capsule for ethical or proprietary products for human or veterinary use. The drug in the capsule embraces any physiologically or pharmacologically active substance that produces a local or a systemic effect. The term physiologically as used herein denotes the administration of a drug to produce normal plasma levels and body functions. The term pharmacologically as used herein denotes variations in response to the amount of drug administered to a drug-receiving host. The phrase drug formulation as used herein means the drug in the capsule is mixed with a pharmaceutically acceptable carrier. The drug includes inorganic and organic compounds without limitation, including drugs that act on the peripheral nerves, adrenergic receptors, cholinergic receptors, nervous system, skeletal muscles, cardiovascular system, smooth muscles, blood circulatory system, synoptic sites, neuroeffector junctional sites, endocrine system, hormone systems, immunological system, organ systems, reproductive system, skeletal system, autocoid systems, alimentary and excretory systems, inhibitory of autocoids and histamine systems, and physiological systems. The active drug that can be delivered for acting on these animal systems includes depressants, beta-blockers, hypnotics, sedatives, psychic energizers, tranquilizers, anti-convulsants, muscle relaxants, antiparkinson agents, analgesics, anti-inflammatories, local anesthetics, muscle contractants, antimicrobials, antimalarials, hormonal agents, contraceptives, sympathomimetics, diuretics, anti-parasitics, neoplastics, hypoglycemics, opthalmics, electrolytes, diagnostic agents, cardiovascular drugs, and the like.

Exemplary drugs that can be in the capsule of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metoprolol tartrate, cimetidine hydrochloride, diphenidol, meclizine hydrochloride, prochlorperazine maleate, phenoxybenzamine, thiethylperazine maleate, anisindone, diphenadione erythrityl tetranitrate, dizoxin, isofumphate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogenic progestational, corticosteroids, hydrocortisone, hydrocorticosterone acetate, cortisone acetate, triamcinolone, methyltesterone, 17 β-estradiol, ethinyl estradiol, ethinyl estradiol 3-methyl ether, prednisolone, 17-hydroxyprogesterone acetate, 19-norprogesterone, norgestrel, norethindone, norethiderone, progesterone, norgesterone, norethynodrel, enitabas, indomethacin, naproxen, fenoprofen, sulidac, diclofenac, indoprofen, nitroglycerin, propranolol, metoprolol, valproate, oxprenolol, timolol, atenolol, alprenolol, cimetidine, clonidine, imipramine, levodopa, chloropmpmazine, reserpine, methyl-dopa, dihydroxyphenylalanine, pivaloyloxyethyl ester of α-methyldopa hydrochloride, theophylline, calcium gluconate ferrous lactate, ketoprofen, ibuprofen, cephalexin, erythromycin, haloperidol, zomepirac, vincamine, diazepam, phenoxybenzamine, β-blocking agents, calcium-channel blocking drugs such as nifedipine, diltiazen, verapamil, and the like. The beneficial drugs are known to the art in *Pharmaceutical Sciences,* edited by Remington 14th Ed., 1979, published by Mack Publishing Co., Easton, Pa; *The Drug, The Nurse, The Patient, Including Current Drug Handbook,* 1974–76, by Falconer, et al., published by Saunder Company, Philadelphia, Pa., and *Medical Chemistry,* $3^{rd}$ Ed., Vol. 1 and 2, by Burger, published by Wiley-Interscience, New York.

The drug can be in various forms, such as uncharged molecules, molecular complexes, pharmacologically acceptable salts such as the hydrochloride, hydrobromide, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides can be used. Also, a drug that is water insoluble can be used in a form that is a water soluble derivative thereof to serve as a solute, and on its release from the device, is converted by enzymes, hydrolyzed by body pH or other metabolic processes to the original biologically active form. The agent including drug, can be present in the capsule with a binder, dispersant, wetting agent, suspending agent, lubricant and dye. The amount of beneficial agent in capsule generally is about from 0.05 ng to 5 g or more, with individual devices containing for example, 25 ng, 1 mg, 5 mg, 125 mg, 250 mg, 500 mg, 750 mg, 1.5 g, and the like.

The pharmaceutically acceptable carrier useful for providing a drug formulation by mixing with a drug are carriers that lend themselves to capsule use and are easily excreted, metabolized, assimilated, or the like by a warm-blooded animal. The carrier medium used for the present purpose can be inorganic, or organic, and of naturally occurring or synthetic origin. Examples of carriers included in the term are substances such as solutions, suspensions, liquids, immiscible liquids, emulsions, sols, colloids, and oils. Representative carriers include liquid alkylene glycols such as ethylene glycol, diethylene glycol, triethylene glycol, ethylene glycol monomethyl ether, liquid polyethylene glycols having a molecular weight of 200, 300, 400 and higher; oils of plants, animal and marine origin, such as corn oil, almond oil, babassu oil, eucalyptus oil, cottonseed oil, palm oil, peanut oil, tung oil, whale oil, herring oil, mineral oil, and the like; emulsions of caster oil in aqueous solutions of pigskin gelatin; emulsions of gum arabic, water and ethyl cellulose; liquid glyceryl triesters of a low molecular weight fatty acid; oils with emulsifiers such as mono- or di-glyceride of a fatty acid; a mixture of from about 70% to about 99.9% propylene glycol and from about 0.1% to 30% of glycerin; a mixture of from about 70% to 99.9% propylene glycol and from about 0.1 to 30% of ethanol; a mixture by volume of from about 80% to 99.9% of propylene glycol and from about 0.1% to about 20% of a mixture of from about 50% to 99.9% of ethanol or glycerin and from 0.1% to about 50% of sterile water; distilled water; 5% dextrose in physiological saline; oils mixed with polyoxyethylene sorbitan monolaurate; a mixture of peanut oil and beeswax; peanut oil containing pectin; glycerine and gelatin, with or without added water; glycerin/castile soap formulation; and the like.

REPRESENTATIVE OF EXAMPLES OF THE INVENTION

Representative of capsules for use in dosage form 10 comprises: a gelatin capsule comprising 50 mg of concentrated ginseng extract formulated with sucrose, palm kernel oil, ascorbic acid, lecithin, natural flavorings, and coloring agents; a gelatin capsule comprising enteric coated pellets of erythromycin including hydroxypropylmethylcellulose and magnesium stearate; a capsule comprising 200 mg of ethchlorvynol blended with glycerin, methylparaben, and polyethylene glycol; a capsule comprising 200 mg of mexiletine hydrochloride formulated with collidal silicon dioxide, corn starch, sodium lauryl sulfate and benzyl alcohol; a capsule comprising 100 mg of phendimetrazine tartrate, silica gel, starch, sucrose and povidone; a capsule comprising 500 mg of cefadroxil monohydrate; a capsule comprising 500 mg of acetaminophen, deionized water, ethylene glycol monoethyl ether, lecithin and sodium propionate; a capsule comprising 25 mg of butalbital and 150 mg of acetaminophen; a capsule comprising fluoxetine hydrochloride, ethyl alcohol, benzoic acid, purified water and sucrose, a capsule comprising 50 mg of butalbital, 325 mg of acetaminophen, and 40 mg of caffeine; a capsule comprising 180 mg of diltiazen hydrochloride; a capsule comprising 37.5 mg of phentermine hydrochloride; a capsule comprising 300 mg of rantidine hydrochloride; and, capsule comprising 1,000 mg of microencapsulated potassium chloride. The dose of therapeautic drug in a capsule is 0.05 to 2 g, with individual capsules containing 25 ng, 1 mg, 5 mg, 125 mg, 250 mg, 500 mg, 750 mg, 1.5 g and the like doses.

A displacement or push composition for use in dosage form 10 can be made according to the following examples: (a) 550 g of sodium carboxymethylcellulose comprising a 700,000 molecular weight, 140 g of hydroxypropylcellulose, comprising a 60,000 molecular weight, 290 g of sodium chloride, and 20 g of ferric oxide are passed through a 40 mesh sieve. These components are mixed for 7 to 10 minutes, and 300 milliliters of anhydrous ethanol is added and the mix sieved through a 20 mesh screen. The blend is air-dried for 20 hours, and then repassed through the 20 mesh screen. Then, 175 mg of the displacement composition is compressed under 2 tons of compression force and placed into the bottom of dosage form 10; (b) a push composition prepared from 415.5 g of a pharmaceutically acceptable poly(ethylene oxide) comprising a 7,500,000 weight average molecular weight, 150 g of sodium chloride and 6 g of colorant ferric oxide are screened through a 40 mesh screen. Then, all the screened ingredients are mixed with 30 g of hydroxypropylmethylcellulose comprising an 11,200 molecular weight to produce a homogenous blend. Next, 300 ml of denatured anhydrous alcohol is added slowly to the blend with continuous mixing for 15 minutes The freshly prepared granulation is passed through a 20 mesh screen, allowed to dry at room temperature 70° F. (22.5° C.) for 16 hours, and again passed through a 20 mesh screen. The screened granulation is mixed with 1.5 g of magnesium stearate on a roller mill for 5 minutes. Next, 240 mg are pressed into a single layered tablet and placed into dosage form 10, followed by a capsule comprising a drug formulation and the dosage form capped that comprises a 25 mil (0.655 mm ) orifice; and (c) an expandable push layer for delivering a drug formulation from dosage form 10 comprises 1375.5 g of poly(ethylene oxide) having a 5,000,000 weight-average molecular weight, 400 g of osmagent potassium chloride, 100 g of hydroxypropylmethylcellulose having a 11,300 molecular weight and 100 g of carboxyvinyl polymer having a 3,000,000 molecular weight, and 20 g of ferric oxide are screened individually through a 40 mesh screen, and then transferred to a mixer. The mixer is run at a low speed for 15 minutes to yield a homogenous blend. Next, 200 ml of ethanol is added to the mixer and the mixing continued for an additional 15 minutes to produce a homogenous wet granulation. The wet granules are screened through a 20 mesh screen, and spread on trays for air-drying for 20 hours. The dried granules are passed through a 20 mesh stainless steel screen, and 4.9 g of magnesium stearate is added thereto and blended to produce lubricated granules. The granules are pressed into a solid layer, 375 mg, comprising 68.75 wt % poly(ethylene oxide), 20 wt % sodium chloride, 5 wt % hydroxypropylmethylellulose, 1 wt % ferric oxide, and 0.25% magnesium stearate. The compressed tablet is placed into dosage form 10.

METHOD OF PRACTICING THE INVENTION

An embodiment of this invention pertains to the use of the dosage form, as provided by this invention, for delivering a drug at a sustained and controlled rate to a human for a therapeutic effect. The method comprises the steps of admitting into the human the dosage form comprising the capsule that comprises a drug formulation, imbibing fluid into the dosage form causing the capsule to dissolve, the displacement composition to expand and push-displace the drug formulation through the orifice over a prolonged period up to 24 hours, to provide therapy.

The dosage form 10 of this invention, as described in this specification, can be used for administering a drug by the oral route, and in another method, it can be sized and shaped for administering drug by the sublingual or buccal routes. The sublingual and buccal routes can be used for quicker therapy, and they can be used to administer a smaller dose of drug. The latter route can be used as a by-pass of the first pass of hepatic metabolism of the drug.

In summary, it will be appreciated that the present invention contributes to the art an unobvious dosage form that possesses practical utility, can administer a drug at a dose metered release rate per unit time. While the invention has been described and pointed out in detail with reference to operative embodiments thereof, it will be understood by those skilled in the art that various changes, modifications, substitutions and omissions can be made without departing from the spirit of the invention. It is intended, therefore, that the invention embraces those equivalents within the scope of the claims which follow.

What is claimed is:

1. A dosage form comprising:
   (a) a wall comprising an injection-moldable composition permeable to the passage of an aqueous fluid which wall is injection molded and forms an internal compartment having a mouth and a bottom;
   (b) a composition in the compartment next to the bottom, said composition comprising a member selected from the group consisting of an osmopolymer and an osmagent, which composition increases in volume in the presence of fluid that enters the compartment; and
   (c) a capsule in the compartment adjacent to the mouth and above the composition, said capsule being free of lamination to the wall.

2. The dosage form according to claim 1, wherein the wall forming the mouth is crimped inward to close the mouth while retaining an orifice in the wall.

3. The dosage form according to claim 1, wherein a snap-in cap closes the mouth while retaining an orifice.

4. The dosage form according to claim 1, wherein the capsule comprises a drug formulation.

5. The dosage form according to claim 1, wherein the wall composition comprises a member selected from the group consisting of a polycaprolactone and a poly(alkylene oxide); a polycaprolactone and a poly(ethylene oxide); a polycaprolactone, a poly(alkylene oxide) and a poly(ethylene glycol); a polycaprolactone and a poly(hydroxypropylcellulose); and a polycaprolactone, a poly(ethylene oxide); a poly(hydroxypropylcellulose) and a poly(ethylene glycol).

6. The dosage form of claim 1 wherein the capsule comprises a body and an engaging cap.

7. The dosage form of claim 1 wherein the capsule comprises a single piece capsule.

* * * * *